United States Patent [19]

Cowan, Jr.

[11] Patent Number: 5,189,014

[45] Date of Patent: Feb. 23, 1993

[54] METHOD OF TREATING CELLULAR FC RECEPTOR MEDIATED HYPERSENSITIVITY IMMUNE DISORDERS

[76] Inventor: Fred M. Cowan, Jr., 21 Shady Brook Dr., Colora, Md. 21917

[21] Appl. No.: 711,709

[22] Filed: Jun. 7, 1991

Related U.S. Application Data

[63] Continuation of Ser. No. 424,088, Oct. 19, 1989, abandoned, which is a continuation-in-part of Ser. No. 911,341, Sep. 25, 1986, abandoned, which is a continuation-in-part of Ser. No. 728,142, Apr. 26, 1985, abandoned, which is a continuation of Ser. No. 204,945, Nov. 7, 1980, abandoned, which is a continuation-in-part of Ser. No. 99,741, Dec. 3, 1979, abandoned.

[51] Int. Cl.[5] .............................................. A01N 37/18
[52] U.S. Cl. .................................................... 514/2
[58] Field of Search ......................................... 514/2

[56] References Cited

U.S. PATENT DOCUMENTS 4,479,934 10/1984 Sedlacek et al. ...................... 424/85

OTHER PUBLICATIONS

Agah et al., *Cancer Research*, vol. 48, Apr. 15, 1988, pp. 2245-2248.
Ainsworth et al., *Cancer*, vol. 61, Apr. 15, 1988, pp. 1495-1500.
Axelrod et al., *Cancer*, vol. 61, Jun. 1, 1988, pp. 2219-2230.
Bender et al., *J. of Infectious Diseases*, vol. 152, Aug. 1985, pp. 405-412.
Berkow, *The Merck Manual of Diagnosis & Therapy*, 1977, pp. 183-255.
Berkow, *The Merck Manual of Diagnosis & Therapy*, 1982, pp. 288-297, 328-347.
Boyle et al., *Bio/Technology*, vol. 5, Jul. 1987, pp. 697-703.
Edelman et al., *The FASEB Journal*, vol. 3, Jan. 1989, pp. 22-30.
Engelman et al., *Cancer Detection and Prevention*, vol. 10, 1987, pp. 435-444.
Engelman et al., *AJP*, Mar. 1985, pp. 367-378.
Fauci, *Science*, vol. 239, Feb. 1988, pp. 617-622.
Fauci et al., *Int. Archs Allergy Appl. Immun.*, vol. 77, (1985), pp. 81-88.
Frank et al., *The New England J. of Medicine*, vol. 300, Mar. 8, 1979, pp. 518-523.
Fraser et al., *The Merck Veterinary Manual*, 1986, pp. 409-424.
Fraser et al., *Structure and Function of Fc Receptors*, 1983, pp. iii-xv and 1-13.
Homsy et al., *Science*, vol. 244, pp. 1357-1360, 1989.
Kerbel et al., *Cell*, vol. 3, Oct. 1974, pp. 105-112.
Kinet et al., *European J. of Clinical Investigation*, vol. 16, 1986, pp. 50-55.

Lange et al., *Aids*, 1987, vol. 1, pp. 155-159.
Liu et al., *Proc. Natl. Acad. Sci. USA*, vol. 81, Oct. 1984, pp. 6471-6475.
MacKinnon et al., *Arthritis and Rheumatism*, vol. 30, May 1987, pp. 498-506.
Jennette et al., *Federation Proceedings*, vol. 141, Mar. 1, 1982, p. 325.
Messerschmidt et al., *J. of Clinical Oncology*, vol. 6, Feb. 1988, pp. 203-212.
Mullins et al., *Nature*, vol. 319, Jan. 1986, pp. 333-336.
Nauts, *Develop. Biol. Standard*, vol. 38, 1978, pp. 487-494.
Old, *Scientific American*, vol. 258, May 1988, pp. 59-75.
Paranjpe et al., *J. of the National Cancer Institute*, vol. 48, Feb. 1972, pp. 563-566.
Ray et al., *Cancer Immunology Immunotherapy*, vol. 18, 1984, pp. 29-34.
Ray et al., *Cancer*, vol. 45, May 15, 1980, pp. 2633-2638.
Ray et al., *Cancer Research*, vol. 42, Dec. 1982, pp. 4970-4974.
Rhodes, *Nature*, vol. 265, Jan. 20, 1977, pp. 253-255.
Rhodes et al., *J. of National Cancer Inst.*, vol. 66, 1981, p. 423.
Roses et al., *Manual of Clinical Immunology*, 2nd. Ed., 1980, pp. 178-211.
Sarin et al., *Science*, vol. 232, May 30, 1986, pp. 1135-1137.
Sinclair, *Immunology Today*, vol. 8, 1987, pp. 76-79.
Sinclair et al., *Clinical Immunology and Immunopathology*, vol. 52 1989, pp. 133-146.
Sjodahl, *Eur. J. Biochem.*, vol. 78, 1977, pp. 471-490.
Stole et al., *Int. J. Cancer*, vol. 14, 1974, pp. 83-92.
Sulica et al., *Sand. J. Immunol.*, vol. 5, 1976, pp. 1191-1197.
Takeda et al., *Science*, vol. 242, Oct. 28, 1988, pp. 580-583.
Tavares et al., *Cancer Research*, vol. 47, 1987, pp. 3190-3194.
Terman, *The New England J. of Medicine*, vol. 305, 1981, pp. 1195-1200.
Tizard, *An Introduction to Veterinary Immunology*, 1977, pp. 81, 98, 108.

*Primary Examiner*—Frederick E. Waddell
*Assistant Examiner*—Gregory Hook
*Attorney, Agent, or Firm*—Milton M. Field

[57] ABSTRACT

A method of immunotherapy for treating diseases and disorders which involve cellular Fc receptor mediated immune responses in humans and animals is disclosed. Abnormal or undesirable cellular Fc receptor mediated immune reactions are beneficially altered by locally or systemically administering an exogenous Fc receptor polypeptide, in particular a multivalent protein having in its molecule several Fc receptor sites, such as staphylococcus protein A, or monovalent Fc receptor possessing only a single Fc receptor site.

13 Claims, No Drawings

METHOD OF TREATING CELLULAR FC RECEPTOR MEDIATED HYPERSENSITIVITY IMMUNE DISORDERS

This is a continuation application of Ser. No. 07/424,088, filed Oct. 19, 1989, now abandoned which is a continuation-in-part application of application Ser. No. 911,341 filed Sep. 25, 1986, now abandoned which is a continuation-in-part of application Ser. No. 728,142 filed Apr. 26, 1985, now abandoned, which is a file wrapper continuation of application Ser. No. 204,945 filed Nov. 7, 1980, now abandoned, which is a continuation-in-part of application Ser. No. 99,741 filed Dec. 3, 1979, now abandoned.

BACKGROUND OF THE INVENTION

The present invention pertains to methods of immunotherapy for treating cellular Fc receptor mediated immune disorders in humans and animal by altering the endogenous Fc receptor mediated immune response in the body by administration of an exogenous polypeptide having a cellular Fc receptor-like binding capability for endogenous antibodies and antibody-antigen immune complexes.

The basic principles of immunology pertaining to immunotherapy are presented in the clinical medical art, for example: *The Merck Manual of Diagnosis and Therapy*, (thirteenth edition, 1977). R. Berkow and J. H. Talbott (eds.), "Immunology Allergic Disorders", pp. 183–156. Merck & Co., Rahway, N.J.; and *Basic & Clinical Immunology* (sixth edition, 1987) D. P. Stites, J. D. Stobo and J. V. Wells (eds.), Appleton & Lange, Los Altos, Calif. These basic principles of immunology are stated as follows.

The human and animal body develops immunity against a variety of invading agents by producing antibody mediated humoral immunity or sensitized cell mediated cellular immunity capable of reacting with and destroying the invading agent. Any agent that can elicit an immune response in the body is called an antigen. Examples of antigens includes: infectious agents, e.g. bacteria and viruses; drugs, e.g. antibiotics; toxins, e.g. chemical substances; foreign tissues, e.g. transplantation antigens; and various self-tissues, e.g. autoimmune antigens, cancer cells, and idiotypes of antibodies. The primary functions of the immune response toward an antigen are recognition, specific response, clearance and memory. In order for the immune system to identify, specify, neutralize and memorize the antigen, immune cells must develop and differentiate to achieve competent cellular and humoral immunity toward the antigen. Regulation or amplification of the immune response in either a positive or negative fashion occurs through cell populations such as T helper and T suppressor lymphocytes and interaction between humoral factors such as antibody, antigen-antibody immune complex, cytokines, e.g. interferons, interleukins, and cellular receptors for those humoral factors, e.g. Fc receptors.

Exposure of a human or animal to a given antigen activates the immune system to develop specific antibodies against the antigen. Antibodies which circulate in the body liquids (humoral immunity) are capable of combining with the antigen forming an antigen-antibody immune complex, wherein the antigen may be inactivated and/or subsequently destroyed. Furthermore, a cellular immunity can be developed by formation of sensitized cells, e.g. sensitized leukocytes, which contain "antibodies", e.g. receptors against the particular antigen, attached to the cell wall and which are capable of combining with the antigen in an immunological reaction and subsequently inactivating and/or destroying it.

Fc Receptors and Fc receptor mediated immunity and immune regulation are well known in the immunological literature, for example: *Structure and Function of Fc Receptors* (1983), A. Froese and F. Paraskevas (eds.), Marcel Dekken, Inc., New York.; Cowan, F. M., et al., 1980, *Biomedicine* 32, 108; and Kerbel, R. S. & Davies, A. J. S., 1974, *Cell* 3, 105. Certain body cells, e.g. lymphocytes and macrophages, possess in their cell walls Fc receptors capable of binding with a specific binding site in the antibody molecule e.g. Fc-fragment, Fc-constant region. Cellular Fc receptors are capable of binding free antibodies and/or antigen-antibody complexes to the cell wall. Cellular Fc receptors may also be secreted and circulate in humoral fluids as "Immunoglobulin binding factors". Cellular Fc receptor mediated immune responses and immunity are regulated by the attachment of free antibodies or immune complexes to the cellular Fc receptors Sinclair, N. R., 1978, *Transplant. Proc.* 10, 349 and Sinclair, N. R. and Panoskaltsis, A., 1987, *Immunol. Today* 8, 76. Since both antigen-antibody immune complex and free antibody compete for attachment to the cellular Fc receptor, the amount and type of free antibodies or immune complexes which become attached and thus the degree of the subsequent cellular Fc receptor mediated immune response may vary dependent on the ratio between free antibodies and antigen-antibody immune complexes and Fc receptors which are present in the given Fc receptor mediated immune reaction.

Antibody binding antigen to the variable antigen-binding site on the Fab portion of the antibody molecule provides antigen specificity; whereas, the antibody Fc constant region engaging Fc receptors activates Fc receptor mediated immunity towards the antigen and transport of antibody across membranes, e.g. delayed hypersensitivity, antibody dependent cellular cytotoxicity (ADCC). *Structure and Function of Fc Receptors*, 1983, A. Froese and F. Paraskevas (eds.), Marcel Dekken, Inc.: New York.); Cowan, F. M., et al., 1980, *Biomedicine* 32, 108. Antigen specific coordination of the immune response to antigen orchestrated by the antigen independent binding of a single molecule, e.g. Fc receptor, explains how a single molecule, e.g. the Fc receptor can control immunity to an infinity of antigens (Sinclair, N. R., 1978, *Transplant. Proc.* 10, 349; Sinclair, N. R. and Panoskaltsis, A., 1987, *Immunol. Today* 8, 76; and provides the opportunity to alter Fc mediated immunity to any antigen, by administering exogenous Fc receptors to change the ratio of endogenous Fc receptors to Fc receptor binding molecules e.g. antibody, antigen-antibody immune complex (Cowan, F. M., et al., 1980, *Biomedicine* 32, 108; Cowan, F. M., et al., 1982, *Biomedicine* 36, 29).

The mechanism of Fc receptor mediated immunity to antigen is constant for all antigens, for example, sheep red blood cell which is a standard test antigen for assaying immunity (present application Examples 1 and 2), (Cowan, F. M., et al., 1979. *Biomedicine* 30, 23), (Cowan, F. M., et al., 1979, *Biomedicine* 30, 241) or antigen of a disease related to the immune response, wherein insufficient immunity to antigen, e.g. cancer cell antigen is known to contribute to the pathology of the disease e.g. adenocarcinoma (present application Example 7), (Cowan, F. M., et al., 1982, *Biomedicine* 36, 29). Therefore, internal use of an exogenous Fc receptor to alter endogenous Fc receptor mediated immunity to antigen is useful in the treatment of diseases related to the immune response, wherein abnormal Fc receptor mediated immunity to antigen contributes to the pathology or symptom of the disease. It (systemic exogenous Fc receptor immune therapy) is the major method of the present invention.

Many pathological disorders in humans and animals involve undesirable or abnormal cellular Fc receptor mediated immune responses, including insufficient or excessive immune responses towards antigens, Cowan, F. M., et al., 1980, *Biomedicine* 32, 108 and Cowan, F. M., et al., 1982, *Biomedicine* 36, 29. Diseases related to the immune response, wherein abnormal immunity to antigen causes or contributes to the pathology or symptoms are documented and described in the clinical medical art. *The Merck Manual of Diagnosis and Therapy* (thirteenth edition 1977) devotes section 2 (pages 183-255) to immunology and allergic disorders; these diseases related to the immune response include: infectious agents, e.g. virus and bacteria; immunodeficiency diseases; hypersensitivity reactions, e.g. delayed hypersensitivity; autoimmune disorders; transplantation; and tumor immunology. Furthermore, the basic principles and participating molecules, e.g. antibody, immune complex, Fc receptors, and cytokines are the same for humans and other mammals, e.g. veterinary and laboratory animals. See *An Introduction To Veterinary Immunology* (1977), Ian R. Tizard; W. B. Saunders Company, Philadelphia; and *Basic & Clinical Immunology* (sixth edition, 1987), D. P. Stites, J. D. Stobo and J. V. Wells (eds.), Appleton & inventionLange, Los Altos, Calif. *The Merck Veterinary Manual* (sixth edition, 1986), C. M. Fraser (ed.), "The Immune System" pp. 409-424, Merck & Co., Rahway, N.J., describes diseases relating to the immune response in animals which correspond with human diseases related to the immune response listed in *The Merck Manual of Diagnosis and Therapy*, (thirteenth edition, 1977). Furthermore, there are "standards tests" for determining immunity to antigen (*The Merck Manual of Diagnosis and Therapy*, thirteenth edition, 1977). Principles for the use of drugs affecting the immune response are described; e.g. as to corticosteriods *Merck Manual*, 1977, states at page 1903: "8. All dosages should be individualized. The effective dose varies with different diseases, with different phases of the same disease, and from patient to patient. 9. The dosage should be kept flexible, being raised or lowered according to alterations in the course of the disease or the development of undesirable effects."

The physiological immune responses are designed to eliminate or neutralize antigens. The formation of antigen-antibody immune complexes is a crucial component in the normal defense of the body again pathogens and other antigens. Under some circumstances, e.g. immune complex disease, immune complexes circulating in the body fluids become pathogenic and may induce inappropriate activation or inactivation of humoral or cellular immunologic effectors. Agnello, V., *Manual of Clinical Immunology*, Rose, N. R. and Friedman H. (eds.), American Society For Microbiology, Washington D.C., p. 178, 1980. Immune complex can also deposit in the tissues of various organs activating effector cells and/or complement, a group of sera proteins that can penetrate and damage cell walls, resulting in the release of substances that produce inflammation and tissue injury. Immune complexes have been associated with glomerulonephritis and vasculites for a wide variety of disease states including bacterial, viral and parasite infections, as well as autoimmune diseases such as rheumatoid arthritis and systemic lupus erythematoses.

Immune complex disease associated with diseases related to the immune response, wherein the immune complex disease causes or contributes to abnormal Fc receptor mediated immunity to disease antigen, e.g. antibody dependent cellular cytotoxicity (ADCC) and delayed hypersensitivity, is documented in the medical art. See Cowan, F. M., et al., 1980, *Biomedicine* 32, 108; *The Merck Manual of Diagnosis and Therapy* (thirteenth edition, 1977, pp. 183-255; Spitler, L. E. p. 200, 1980, *Manual of Clinical Immunology*, Rose, N. R. and Friedman H. (eds.), American Society For Microbiology, Washington D.C. Clinical tests to determine immune complex and Fc receptor mediated immunity are available and described in the clinical medical art. These include the ADCC assay (Example 1 of the present application). See Schur, P. H., p. 193, 1980, *Manual of Clinical Immunology*, Rose, N. R. and Friedman H. (eds.), American Society For Microbiology, Washington D.C. Immune-complexes consisting of tumor antigens and antibodies have been identified in the sera of patients with various malignancies. There is convincing evidence that tumor antigen-antibody complexes interfere with the lymphocyte functions that would normally destroy the tumor cells Cowan; F. M., et al., 1979, *Biomedicine* 30, 23; Messerschmidt et al., 1988, *J. Clin. Oncol.*, 6, 487.

An association between bacterial infection, or immunotherapy with bacterial products, and tumor regression is described in the medical art (Old, L. J., 1988, *Scientific American* 258, 59; Cowan, F. M., et al., 1980, *Biomedicine* 32, 108; Nauts H. C., 1977, *Develop. Biol. Standard* 38, 487). This association may be summarized as follows: For centuries spontaneous tumor regressions have been associated with microbial infection, principally Staphylococcal and Steptococcal. Bush, in 1868, documented spontaneous tumor regression occurring in patients with erysipelas infection due to Streptococcal organisms. Dr. William Bradley Coley, a surgeon at Memorial Hospital in New York, from 1897-1931, treated cancer patients with microbial products and achieved numerous remissions of a variety of cancers. "Coley's toxins" consisted of a mixture of two microbes, *Streptococcus pyogenes* and *Serratia marcescens*. Although Dr. Coley results were dramatic, with remissions of histologically confirmed inoperable cancers, the crude bacterial preparations and lack of knowledge of the immune system prevented identifying the active components and mode of anticancer action.

A "rational basis" for the antineoplastic activity of Coley's toxins can be presented based on contemporary knowledge of cytokine and Fc receptor immunotherapy. Coley may have nearly a century past used a form of combined cytokine-Fc receptor synergistic immunotherapy. Interferons (IFN), Interleukins (IL) and tumor necrosis factor (TNF) are cytokines and all three substances have displayed individual anticancer activity in human clinical trials (Old, L. J., 1988, *Scientific American* 258, 59), (Ravin, A., et al., 1988, *Can. Res.*, 48, 2245), (McIntosh, J. K., et al., 1989, *Can. Res.*, 49, 1408). Furthermore, when used in combination against mouse sarcoma metastatic tumors, as a immunotherapeutic prototype for human clinical trials, they display synergism in that the cytokines are much more effective, even at lower nontoxic doses, used in combination than individually (Ravin, A., et al., 1988, Can. Res., 48, 2245), (McIntosh, J. K., et al., 1989, Can. Res., 49, 1408).

The injection of combined Serratia marcescens and Streptococcus pyogenes microbial products have induced IFN and IL in cancer patients (Axelrod, R. S., et al, 1988, Cancer 61, 2219). The Serratia marcescens the gram negative microbial component of Coley's toxins contains lipopolysaccharide (LPS), the most potent inducer of TNF (Old, L. J., 1988, Scientific American 258, 59), and peptidoglycans, which contain muramyl peptides which are associated with IL-like activity (Chedid, L., 1986, Fed. Proceed., 45, 2531), (Kotani, S., et al, 1986, Fed. Proceed., 45, 2534). LPS (Old, L. J., 1988, Scientific American 258, 59) and muramyl peptide (Chedid, L., 1986, Fed. Proceed., 45, 2531) have demonstrated individual and combined synergistic antineoplastic activity (Fuks, B. B., et al., 1987, Byulleten' Eksperimental'noi Biologii i Meditsiny, 104, 497); furthermore, both LPS and muramyl peptide induce the cytokines INF and TNF with their combined action on INF and TNF production being synergistic (Kotani, S., et al., 1986, Fed. Proceed., 45, 2534), (Fuks, B. B., et al., 1987, Byulleten' Eksperimental'noi Biologii i Meditsiny, 104, 497). INF, IL, and TNF combined cytokine immunotherapy may explain the antineoplastic action of the Serratia marcescens component of Coley's toxins.

The major antineoplastic component of Coley's toxins *Streptococcus pyogenes*, and certain other gram positive microbes such as *Staphylococcus aureus*, in addition to muramyl peptides (Kotani, S., et al, 1986, Fed. Proceed., 45, 2534) associated with IL-like activity, contain in their cell walls proteins which bind the Fc constant region of antibody, e.g. exogenous Fc receptors (Boyle, M. P. D., and Reis, K. J., 1987, Bio/Technology 5, 697). Cytokines, e.g. interferon, enhance Fc receptor expression amplifying Fc receptor mediated immunity (Cowan, F. M., et al., 1982, Biomedicine 36, 29), and Fc receptors, engaged by antibody Fc constant region ligand, function as signal transducing molecules which promote gene expression and production of cytokines (Cassatella, M. A., et al., 1989, J. Exp. Med., 169, 549) indicating a Fc receptor-cytokine immune regulatory loop. A Fc receptor-cytokine immune regulatory loop provides a "rational basis" for the synergistic actions of the cytokine inducing and microbial Fc receptor components of Coley's toxins. The implications that Coley's toxins contained immunotherapeutic bacterial molecules such as muramyl peptide and LPS that either mimic or induce a variety of cytokines and bacterial Fc receptor which acted in a synergistic fashion to stimulate the bodies immune response to destroy cancers provides the medical art with a historical "rational basis" for bacterial product, e.g. microbial Fc receptor, muramyl peptides, LPS or combination of bacterial products for immunotherapy of cancer. It is a particular advantage of the present invention that exogenous Fc receptor systemic immunotherapy can be used in conjunction with other immune modulators such as microbial products or cytokines to achieve synergistic immunotherapy.

Several studies concerning the influence of staphylococcus aureus protein A (which in the following will be abbreviated as SPA) on immune-reactions have been made and a variety of contradictory in vitro results have been reported. These include activation of ADCC (Sulica, A., et al., 1976, Scand. J. Immunol., 5, 1192), inhibition of ADCC (Rossenblatt, J., et al., 1977, J. Immunol. 118, 981), mitogenic activity (Forsgren, A., Eur. J. Immunol., 1976, 6, 207-218, and anti-mitogenic activity (Williams, R. C. and Kronvall, G., 1972, Proc. Soc. Exp. Biol. Med., 139, 480). The publications of Cowan et al. harmonizes these contradictory results described in the prior scientific art and present the concept of exogenous Fc receptor systemic immunotherapy, for example: (1) The augmentation or inhibition of ADCC by SPA in vitro was shown to be due to the relative ratio of antibody, immunecomplex and Fc receptor (1979, Biomedicine 30, 23), (present application Example 1). (2) SPA augments or inhibits immunity, e.g. delayed hypersensitivity to antigen, such as SRBC in vivo (1979, Biomedicine 30, 241), (present application Example 2). (3) The mitogenic and antimitogenic activity of SPA is due to the Fc receptor valence (1979, Biomedicine 31, 220), (present application Example 3). (4) A review article explaining the use of exogenous Fc receptors to alter endogenous Fc receptor mediated immunity (1980, Biomedicine 32, 108). (5) systemic SPA Immunotherapy of rat adenocarcinoma (1982, Biomedicine 36, 29). (present application Example 7). *Staphylococcus aureus* Cowan I whole bacteria has been used in vitro to remove "blocking activity" from tumor-bearer sera (Steele, G., et al., 1975, Int. J. Cancer 15, 180), and ex vivo on affinity columns (extracorporeal perfusion) to treat a single colon carcinoma patient (Bansal S. C., et al., 1978, Cancer 42,1); however, no systemic, e.g. oral or parenteral, in vivo pharmaceutical use of SPA has been suggested prior to the publications of Cowan et al. The systemic exogenous Fc receptors immunotherapy, the method of the present invention, provides a particular advantage over the more expensive and invasive ex vivo extracorporeal perfusion immunotherapy.

Pollard U.S. Pat. No. 4,464,164. Oct. 11, 1983) teaches that the ex vivo extracorporal Fc-reagents can be used to retard the growth of neoplasts in subject mammals and the utility for the use of an extracorporeal Fc-reagent to retard the growth of neoplasts is established by reference to published prior art (col. 1, lines 9–19). The advantage over the prior blood processing art claimed in the Pollard patent is that no separation of plasma from other blood elements is required which reduces the complexity of the extracorporal procedure (col. 1, lines 36–41). Systemic SPA immunotherapy, the method of the present application, completely eliminates the expensive and invasive extracorporeal procedure and therefore constitutes a great advantage over the prior SPA ex vivo immunotherapy.

Sedlacek et al U.S. Pat. No. 4,479,934 teaches the injection of complement or antibody Fc-reagents for the treatment of immune complex disease. These endogenous Fc receptors produced within the body differ from the exogenous Fc receptors of the present invention which are produced outside the body, e.g. microbial Fc receptors.

SUMMARY OF THE INVENTION

The present invention pertains to methods of immunotherapy for treating cellular Fc receptor mediated immune disorders in humans and animals by altering the endogenous Fc receptor mediated immune response in the body by administration of an exogenous polypeptide having a cellular Fc receptor-like binding capability for endogenous antibodies and antibody-antigen immune complexes.

It is an object of the present application to provide a method of immunotherapy for treatment of cellular Fc receptor mediated immune disorders, which contribute to the pathology or symptoms of diseases related to the immune response, in humans and animal; wherein, abnormal endogenous Fc receptor mediated immunity involves a pathological ratio of endogenous Fc receptor to Fc receptor binding molecules, e.g. antibody, immunecomplex, by systemic internal, e.g. oral, parenteral, administration of an effective dose of an exogenous polypeptide having a cellular Fc receptor-like binding capability for endogenous antibodies and antibody-antigen immune complexes, thus directly or indirectly restoring normal Fc receptor mediated immunity and overcoming the immune disorder.

It is a further object of the present invention to provide such a method, wherein the abnormal cellular Fc receptor mediated immune reaction to disease antigens, which contribute to the pathology or symptoms of diseases related to the immune response, is enhanced by inhibiting or reducing the inhibitory effect of antigen-antibody immune complexes, e.g. immunecomplex disease, which interfere with the normal cellular Fc receptor mediated immune reaction by systemic administration of an effective dose of an exogenous polypeptide having a cellular Fc receptor-like binding capability for endogenous antibodies and antibody-antigen immune complexes, thus directly or indirectly restoring normal Fc receptor mediated immunity and overcoming the immune disorder.

It is a further object of the present invention to provide such a method wherein an undesirably strong abnormal cellular Fc receptor mediated immune response or autoimmunity, which contribute to the pathology or symptoms of diseases related to the immune response, is reduced by inhibiting or reducing the formation of sensitized cell by preventing free antibodies or immune complexes from attaching to the cellular Fc receptors by systemic administration of an effective dose of an exogenous polypeptide having a cellular Fc receptor-like binding capability for endogenous antibodies and antibody-antigen immune complexes, thus directly or indirectly restoringnormal Fc receptor mediated immunity and overcoming the immune disorder.

In order to accomplish the foregoing objects, there is provided according to the present invention a method of immunotherapy for altering abnormal cellular Fc receptors mediate immune reactions to disease antigens, which contribute to the pathology or symptoms of diseases related to the immune response in humans and animals; which comprises administering to a human or animal patient an effective amount of an exogenous polypeptide, which has in its molecule at least one portion possessing a binding capability for the Fc constant region of an antibody or antigen-antibody immune complex. In particular, there is provided a method for treating disorders involving abnormal cellular Fc receptor mediated immune reactions in human or animal patients which comprises administering to a human or animal in need of such treatment an amount of said exogenous polypeptide which is effective in adjusting the Fc receptor mediated regulation of the immune reaction in a manner suitable to overcome said disorder.

DETAILED DESCRIPTION OF THE INVENTION

Physiological disorders and diseases wherein undesirable or abnormal cellular Fc receptor mediated immune responses to disease antigens, associated with diseases related to the immune response, are the essential cause or play an important contributing role are well known in the medical art.

It has been found that exogenous polypeptides which contain in their molecule at least one binding site capable of binding to the Fc portion of immunoglobulin antibodies or immune complexes of antigens with such antibodies are useful in the treatment of such disorders or diseases, in particular in the treatment of such disorders and diseases wherein the immune response is influenced by endogenous Fc receptors, circulating immune complexes e.g. immune complex disease, a disease recognized in both the medical and patent art, cellular gene expression or complement fixation. In the following these exogenous polypeptides which are produced externally outside the body will be designated as "exogenous Fc receptors" or Fc-reagents such as microbial Fc receptors e.g. viral or bacterial Fc receptors.

Exogenous Fc receptors which are suitable as the pharmacologically active ingredient in the method according to the present application include naturally occurring proteins, in particular glycoproteins, which contain in their molecule one or several, e.g. between one and about 10 Fc-receptor sites. Exogenous Fc receptor proteins usually are elongated substantially straight chain proteins having a molecular weight of from about 5,000 to about 200,000 (Boyle, M. P. D. and Reis, K. J., 1987, *Bio/Technology* 5, 697).

The binding properties of exogenous Fc receptor proteins of different origins towards various classes of immunoglobulins may vary (Boyle, M. P. D. and Reis, K. J., 1987, *Bio/Technology* 5, 697). Of particular interest for the method of the present application are those Fc receptor proteins which bind to the major classes of antibodies and have a greater affinity for complexed or agglutinated antibodies, that is immune complexes, than for free antibodies. Such proteins are found, for example, in certain streptococcal or staphylococcal bacteria e.g. bacterial Fc receptors, red blood cells, placenta membranes, leukocyte membranes and cells infected with herpes simplex virus (Cowan, F. M. et al., 1980, *Biomedicine* 32, 108). Particularly suitable sources are the cell walls of staphylococcus aureus, leukocyte in cell culture or non-lymphoid cells infected with herpes simplex virus in cell culture. The proteins can be produced from these sources by conventional methods. Microbial or bacterial sources are preferred, because the proteins are more easily isolated and purified from these sources. A preferred exogenous Fc receptor protein is *Staphyloccus aureus* protein A (SPA), a cell wall component of *Staphylococcus aureus*, which is commercially available (Pharmacia, Piscataway, N.J.). Exogenous Fc receptors can be produced commercially by known methods, e.g. conventional fermentation processes (Pharmacia, Piscataway, N.J.), recombinant DNA technology (Repligene Cambridge, Mass.) or amino acid synthesis.

The body's immune system contains its own mechanisms for regulating immune responses and avoiding over reaction. Binding of immune complexes to cellular Fc receptors is one major mechanism of the body's immune regulation (Cowan, F. M. et al., 1980, *Biomedicine* 32, 108). Immune complexes Fc receptor interaction plays an important role in induction and maintenance of the body's immune tolerance and response to antigen. The immune mechanisms underlying the reactions by which the single molecule, namely, the exogenous Fc. receptor, can effect both immune and gene regulation, thus influencing immune-response related disorders and diseases have now been clarified. Based on this understanding, a method for efficiently using exogenous Fc receptors in immunotherapy has been designed.

It has now been found that administration of exogenous Fc receptors can alter cellular Fc receptor mediated immune reactions to disease antigens (present application Example 7; Cowan, F. M. et al., 1982, *Biomedicine* 36, 29), associated with diseases related to the immune response wherein immune complexes participate as a co-factor in immunological interactions, including immune complex interactions with immune regulatory cells effective in positive or negative immune regulation, e.g. in thymus T cell helper and T cell suppressor systems, in that the exogenous Fc receptors react with immune complexes and thus prevent or neutralize their participation in the immune reaction (present application Example 2), (Cowan, F. M. et al., 1979, *Biomedicine* 30, 241). Furthermore, the Fc receptors can react with the free antibodies and thus prevent their attachment to the endogenous cellular Fc receptors (present application Example 1; Cowan, F. M. et al., 1979, *Biomedicine* 30, 23).

The immune response and specifically the delayed hypersensitivity response which is a synonym for T cell regulated cell-mediated immunity (*The Merck Manual of Diagnosis and Therapy*, (thirteenth edition, 1977), R. Berkow and J. H. Talbott (eds.), "Immunology Allergic Disorders", p. 183-156. Merck & Co., Rahway, N.J.) is known to be of central importance in a variety of disease states related to immunity including autoimmune disease, immune deficiency disease, malignancies and infectious agents e.g. bacterial, viral, fungal and parasite infections. According to the present application, the competitive binding of exogenous Fc receptors to immune complexes or free antibodies is therapeutically used in vivo to regulate the immune responses. In antigen specific immune regulation, e.g. delayed hypersensitivity reactions, involving T cell helper and T cell suppressor systems communication between different cell populations can be effected by antigen-antibody immune complexes cross-linking cellular Fc receptors on regulatory cells to antigen receptor sites on antigen presenting cells, e.g. macrophages. Binding of substantial portions of the immune complex by exogenous Fc receptor can competitively inhibit both T cell helper and T cell suppressor functions (present application Example 2), (Cowan, F. M. et al., 1979, *Biomedicine* 30, 241).

It has been found that administration of an exogenous Fc receptor can be therapeutically used to diminish or block in vivo the immune complex participation in endogenous Fc receptor mediated immune regulation (present application Example 2), (Cowan, F. M. et al., 1979, *Biomedicine* 30, 241; Cowan, F. M. et al., 1980. *Biomedicine* 32, 108). Administration of an exogenous Fc receptor can be used to maintain the cellular Fc receptor mediated primary delayed hypersensitivity response against an antigen within desirable and physiologically acceptable limits by administering an amount of the exogenous Fc receptor which is sufficient to bind such portion of the immune complex and/or antibody the formation of which is caused by the sensitizing antigen, that a ratio of immune complex to antibody is adjusted to achieve the desired degree of delayed hypersensitivity response. The suitable amount of exogenous Fc receptor will vary of course depending on the amount of free antibody or antibody-antigen immune complex and Fc receptors which are present. Thus administration of an exogenous Fc receptor can considerably alter the antigen specific primary delayed hypersensitivity response of the body to a subsequent contact with the respective antigen.

In view of the foregoing, it is self-evident that the effect of administration of an exogenous Fc receptor on immune reactions will vary considerably depending on the type and amount of immunologically active participants e.g. Fc receptors, antibodies, immune complex which are involved in the respective immune reaction. Thus, administration of exogenous Fc receptors can be used to enhance immune complex hampered insufficient cellular Fc-receptor mediated immune response by administering an amount of Fc receptor which is sufficient to bind all or a substantial portion of the inhibitory immune complexes, with no or only minimum excess available for binding free antibodies. The binding of protein A to the Fc-portion of antigenantibody immune complexes effectively prevents in a competitive reversible reaction subsequent binding of these complexes to cellular Fc receptors. By altering the immune complex interaction with Fc receptors, the rate of attachment of free antibodies to the cellular Fc receptors can be enhanced. Administration of exogenous Fc receptors can also be used to suppress undesired or excessive cellular Fc receptor mediated immune response by administering an amount of the exogenous Fc receptor which is sufficient to bind a substantial portion of the free antibodies or immune activating immune complex, thus reducing the rate of attachment of free antibodies or immune activating immune complex to the cellular Fc receptor.

Exogenous Fc receptor proteins can be obtained by known methods, e.g. bacteria, enzyme digestion of SPA, containing only one Fc receptor site per molecule (Cowan, F. M. et al., 1980, *Biomedicine* 32, 108), (Boyle, M. P. D. and Reis, K. J., 1987, *Bio/Technology* 5, 697). Such monovalent Fc-receptors are particularly useful for inhibiting undesirable complement fixation or gene expression (present application Example 6), (Cowan, F. M. et al., 1979, *Biomedicine* 30, 23). Monovalent exogenous Fc receptors, have been found to be effective in counteracting the action of mitogenic agents by suppressing gene expression and DNA synthesis which is normally elicited by these mitogens (present application Example 3), (Cowan, F. M. et al., 1979, *Biomedicine* 31, 220. Thus, it is reasonable to conclude that monovalent exogenous Fc receptors functioning as a repressor of DNA synthesis (Cowan, F. M. et al., 1980, *Biomedicine* 32, 108) in mitogen activated leukocytes and malignant cell lines create a "cytostatic state" in which the growth of malignant cells is reduced or arrested. Additionally, in the "cytostatic state" induced by the monovalent exogenous Fc-receptors the resistance of cells to infections by viruses which require cellular DNA-synthesis for their replication is increased. Administration of monovalent exogenous Fc receptor can further be used to counteract the action of viral, malignant or autoimmune mitogens and administering an effective amount of the monovalent exogenous Fc receptor is effective in suppressing the gene expression and DNA synthesis which is elicited in viral replication mitogens.

Multivalent exogenous Fc receptors which are capable of attaching a plurality of antibodies may activate the complement system inducing an allergic reaction (Cowan, F. M. et al., 1979, *Biomedicine* 30, 23), (Cowan, F. M. et al., 1982, *Biomedicine* 36, 29). For example multivalent exogenous Fc receptors can cause anaphylaxis-like cutaneous and systemic reactions in nonimmunized guinea pigs and cutaneous reactions in humans. Avoidance of exogenous Fc receptor mediated anaphylactic reactions can be achieved by administering a combination of multivalent and monovalent exogenous Fc receptors or only monovalent Fc receptors. Equally monovalent exogenous Fc receptors have been found effective in reducing the severity of disorders mediated by complement interaction with cellular Fc receptor-mediated immune responses (present application Example 6; Cowan, F. M. et al., 1979, *Biomedicine* 30, 23), (Cowan, F. M. et al., 1982, *Biomedicine* 36, 29).

Administration of monovalent Fc receptors in combination with multivalent Fc receptors can be used to avoid the possibility of complement-mediated side effects and increase their physiological compatibility.

Administration of a monovalent or a combination of a monovalent and a multivalent exogenous Fc receptor is preferred under most circumstances; however, administration of a multivalent Fc receptor is particularly indicated for promoting the healing of wounds, surgical incisions, broken bones and regeneration of bones which have been associated with bacterial product, e.g. Coley's toxins therapy (Nauts, H. C., 1977, *Develop. Biol. Standard* 38, 487). The mitogenic side effect of a multivalent Fc receptor and production of cytokine e.g. interferon associated with exogenous Fc receptor (Cowan, F. M. et al., *Biomedicine* 36, 29) contributes to the enhancement of wound-healing and bone-regenerating. Furthermore, administration of the multivalent exogenous Fc receptor is effective in relieving pain which has been observed associated with bacterial product e.g. Coley's toxins therapy (Nauts, H. C., 1977, *Develop. Biol. Standard* 38, 487). This pain-relieving activity is believed to be due to Fc receptor binding of B-endorphines as indicated by the cross reactivity between the amino acid sequence of the Fc-antibody portion of antibody and B-endorphines. Furthermore, administration of multivalent exogenous Fc receptors could enhance the regression of local solid tumors and infectious agents due to complement mediated damage. The use of cytotoxic agents bound to antibody is well known in the medical art (*Antibody-Mediated Delivery Systems*, 1988, J. D. Rodwell (ed), Marcel Dekker) and multivalent Fc receptors can be coupled by known methods to antitumor antibodies e.g. monoclonal antibodies which bind to cancer cell membranes where the Fc-reagent binds endogenous antibody inducing complement mediated cell lysis or activates endogenous Fc receptor mediated effector cells e.g. ADCC, phagocytosis.

Suitably exogenous Fc receptors are administered internally, preferably orally, or parenterally to a patient in need of such treatment, but can be administered locally if required. Methods for administering drugs are described in the medical art (*The Merck Manual of Diagnosis and Therapy*, (thirteenth edition, 1977), R. Berkow and J. H. Talbott (eds.), Clinical Pharmacology, pp. 1781–1948. Merck & Co., Rahway, N.J.). Suitably compositions for internal administration may comprise conventional pharmaceutical carriers, and may further comprise pharmaceutical adjuvants, e.g. binders, monoclonal antibodies, liposomes, etc. The route of administration is not critical being well known in the medical art, suitable compositions for internal administration include solutions for subcutaneous, intravenous, intradermal or intraperitoneal injection, which due to the microenvironment of the peritoneal cavity can be a preferred route for administering immunotherapeutic agents (Ravin, A., et al., 1988, *Can. Res.* 48, 2245). Suitable injection solutions contain an effective dose of the exogenous Fc receptor dissolved or suspended in a conventional physiologically acceptable sterile diluent. The administered doses can vary considerably depending on the type of the compound, the animal, the mode of administration, the treated conditions, e.g. the disease and/or the individual status of a patient at a given time, and the therapy which is desired. Usually, satisfactory results are obtained with dosages between about 1 ng and about 1 g/1 kg body weight. The dose can be if needed determined by standard clinical tests for measuring the patient's serum levels of immune complexes and/or Fc receptors, e.g. ADCC assay (Example 1 of the present application); (Schur., P. H., p. 193, 1980, *Manual of Clinical Immunology*. Rose, N. R. and Friedman H. (eds.). American Society For Microbiology, Washington D.C.) and calculating the dose based on the relative concentrations of these substances.

Exogenous Fc receptor treatment of diseases related the immune response, wherein circulating immune complexes contributing to pathology or symptoms of the disease, the level of circulating immune complexes is determined as required, e.g. daily, and the dose of exogenous Fc receptor is specifically calculated which is suitable to substantially neutralize the determined concentration of circulating immune complexes. In this manner, a high degree of safety and predictability of the therapeutic effect is achieved. Clinical immunological test procedures for determining the concentration of antibody, Fc receptor proteins and/or circulating immune complexes in body liquids, e.g. in serum, and for accessing Fc receptors mediated immunity, e.g. delayed hypersensitivity, ADCC, in a patient are well known in the medical art (Examples 1 and 2 of the present application), (Schur., P. H., p. 193, 1980, *Manual of Clinical Immunology*, Rose, N. R. and Friedman H. (eds.). American Society For Microbiology, Washington D.C.), (*The Merck Manual of Diagnosis and Therapy*, (thirteenth edition, 1977), R. Berkow and J. H. Talbott (eds.), "Immunology Allergic Disorders", p. 183–156. Merck & Co., Rahway, N.J.). Furthermore, if desired, the Fc receptor protein which is most effective in reacting with the respective immune complex can be determined. In vitro tests can also be performed in accordance with conventional test methods in order to elicit the dose of monovalent Fc receptor which is needed at a given time to suppress gene expression (present application Example 3), (Cowan, F. M. et al., 1979, *Biomedicine* 31, 220) or complement mediated disorders (present application Example 6), (Cowan, F. M. et al., 1979, *Biomedicine* 30, 23) in accordance with the given condition of a patient, in order to provide efficacy to the Fc receptor mediated gene regulatory treatment or complement fixation treatment according to the present invention. It is a particular advantage of the method according to the present invention that treatment with exogenous Fc receptors is substantially void of harmful side effects.

According to a specific embodiment of the present invention, there is provided a method of immunotherapy for treatment of cellular Fc receptor mediated immune disorders, which contribute to the pathology or symptoms of diseases related to the immune response, in humans and animal patients; wherein, abnormal endogenous Fc receptor mediated immunity involves a pathological ratio of endogenous Fc receptor to Fc receptor binding molecules, e.g. antibody, immune complex, by local or systemic, e.g. oral, parenteral, administration of an effective dose of an exogenous polypeptide having a cellular Fc receptor-like binding capability for endogenous antibodies and antibody antigen immune complexes, thus directly or indirectly restoring normal Fc receptor mediated immunity and overcoming the immune disorder.

According to a specific embodiment of the present invention, there is provided a method of immunotherapy for treating or alleviating the symptoms of an immune complex disease, in a patient suffering from such a disease which method comprises local by or systemically administering to said patient an effective dose of an exogenous Fc receptor which reacts directly or indirectly with the Fc portion of antibody or immune complex causing said immune complex disease.

According to a specific embodiment of the present invention, there is provided a method of immunotherapy for treatment or alleviating the symptoms of a disease related to the immune response, that is an infectious disease, e.g. bacterial, viral, fungal or parasite, in a patient suffering from such a disease, wherein abnormal Fc receptor mediated immunity to the invading antigen contributes to the pathology or symptoms of the disease, which method comprises administering to said patient an effective dose of an exogenous Fc receptor which reacts directly or indirectly with the Fc portion of antibody or immune complex, causing the abnormal Fc receptor mediated immunity to the invading antigen, enhancing the body's own endogenous cellular Fc receptor mediated immune response and overcoming the abnormal Fc receptor mediated immunity to the invading infectious disease antigen. The amount of exogenous Fc receptor is preferably sufficient to bind directly or indirectly a substantial portion of the antigenantibody immune complex formed in the body with binding substantially none or only a minor amount of the free antibodies formed in response to the antigen invasion.

According to a specific embodiment of the present invention, there is provided a method of immunotherapy for treatment or alleviating the symptoms of a disease related to the immune response, that is a neoplastic disease e.g. cancer/malignancy, in a patient suffering from such a disease, wherein abnormal Fc receptor mediated immunity to the invading antigen contributes to the pathology or symptoms of the disease, which method comprises administering to said patient an effective dose of an exogenous Fc receptor which reacts directly or indirectly with the Fc portion of antibody or immune complex enhancing the body's own endogenous cellular Fc receptor mediated immune response and overcoming the abnormal Fc receptor mediated immunity to the invading neoplastic antigen.

According to a specific embodiment of the present invention, there is provided a method of immunotherapy for treating carcinoma which comprises enhancing the body's own endogenous cellular Fc receptor mediated immune response towards the invading antigen by administering an effective amount of an exogenous Fc receptor.

According to a specific embodiment of the present invention, there is provided a method of immunotherapy for treating adenocarcinoma which comprises enhancing the body's own endogenous cellular Fc receptor mediated immune response towards the invading antigen by administering an effective amount of an exogenous Fc receptor.

According to a specific embodiment of the present invention, there is provided a method of immunotherapy for treating mammary adenocarcinoma which comprises enhancing the body's own endogenous cellular Fc receptor mediated immune response towards the invading antigen by administering an effective amount of an exogenous Fc receptor.

According to another embodiment of the present invention, there is provided a method of immunotherapy for treating or alleviating the symptoms of a disease related to the immune response, that is, transplant rejection in a patient undergoing an organ or tissue transplant, wherein abnormal Fc receptor mediated immunity to the transplantation antigen contributes to the pathology or symptoms of the disease, which comprises administering an effective immuno-suppressive amount of an exogenous Fc receptor which is capable of binding antibodies or immune complexes formed in response to the foreign graft providing an immuno-suppressive effect on the cellular Fc-receptor mediated graft rejection and preventing the formation of sensitized lymphocytes.

According to another embodiment of the present invention, there is provided a method of immunotherapy for treating or alleviating the symptoms of a disease related to the immune response, that is, an autoimmune diseases wherein the body has developed an immunity against some of its own tissue proteins and abnormal Fc receptor mediated immunity to the disease antigen contributes to the pathology or symptoms of the disease. Examples of such autoimmune diseases include multiple sclerosis, myasthenia gravis, pernicious anemia, Addison's disease, Goodpasture's disease, systemic lupus erythematosus, rheumatoid arthritis. Treatment and/or prophylaxis of these autoimmune diseases according to the present invention comprises administering to a patient in need of such treatment an immuno-suppressive effective amount of an exogenous Fc receptor, which is capable of binding antibodies or immune complexes produced as part of the bodies autoimmune response and preventing the formation of sensitized lymphocytes by antibodies or immune complexes.

According to another embodiment, there is provided a method for improving the compatibility of drugs which can cause allergic side reactions due to complement interaction with a cellular Fc receptor mediated immune response e.g. anaphylaxis. In the case of a combination of an exogenous multivalent Fc receptor with an exogenous monovalent Fc receptor, the ratio between monovalent and multivalent Fc receptors is in the range of from about 1:1 to about 10:1.

According to another embodiment of the present invention, there is provided a method of immunotherapy for reducing the severity of diseases which are caused by complement interaction with a cellular Fc receptor mediated immune response, such as glomerulonephritis or anaphylaxis which comprises administering an effective amount of an exogenous monovalent Fc receptor, which is sufficient to interfere with the attachment of antibodies on lymphocytes in a pattern which enhances complement interaction.

Local injection or application of Fc receptor is suitable for monovalent Fc receptor to reduce local inflammation, multivalent Fc receptor to induce local inflammation in solid tumors e.g. SPA-monoclonal antibody, multivalent Fc receptor to induce mitogenesis (cell division) to speed healing of wounds or bones and Fc receptor to interact with B-endorphins to reduce pain.

According to a specific embodiment of the present invention, there is provided a method of immunotherapy for treatment or alleviating the symptoms of a disease related to the immune response, that is a immune deficiency diseases, for example AIDS, FAIDS, in a patient suffering from such a disease, wherein abnormal Fc receptor mediated immunity to invading antigen contributes to the pathology or symptoms of the disease, which method comprises administering to said patient an effective dose of an exogenous Fc receptor which reacts directly or indirectly with the Fc portion of antibody or immune complex enhancing the body's own endogenous cellular Fc receptor mediated immune response and overcoming the abnormal Fc receptor mediated immunity to the invading antigen.

According to specific embodiment of the present invention there is provided a method of immunotherapy for treatment and alleviating the symptoms of immune deficiency diseases, for example AIDS, FAIDS, which comprises administering an effective amount of an exogenous Fc receptor which is sufficient to substantially neutralize the high levels of circulating immune complexes e.g. immune complex disease associated with these diseases. An immune deficiency disease of particular interest is acquired immunodeficiency syndrome (AIDS) induced by an infectious agent e.g. retrovirus, the human immunodeficiency virus. The pathology and symptoms of AIDS are known to involve immune complex, reduced delayed hypersensitivity and defective Fc receptor function.

A key role has been ascribed to Fc receptor mediated immunological communication and gene expression which influences immune regulation, cellular differentiation, malignant transformation and viral replication (Cowan, F. M. et al., 1980, *Biomedicine* 32, 108) (Cowan, F. M. et al., 1982, *Biomedicine* 36, 29). Abnormal Fc receptor mediated immunity contributes to the pathology of diseases associated with defective immunity e.g. cancer and AIDS. Therefore, microbial Fc receptors such as SPA are useful immunopharmological agents to alter the relative ratio of humoral factors interacting with leukocyte cellular Fc receptors from pathological to physiological concentrations restoring normal Fc receptor mediated immunity provided a method of immunotherapy for treatment or alleviating the symptoms of a disease related to the immune response.

In order to accomplish the foregoing objects, there is provided according to the present invention a method of immunotherapy for altering abnormal cellular Fc receptors mediated immune reactions to disease antigens, which contribute to the pathology or symptoms of diseases related to the immune response in humans and animals; which comprises administering to a human or animal patient an effective amount of an exogenous polypeptide, which has in its molecule at least one portion possessing a binding capability for the Fc constant region of an antibody or antigen-antibody immune complex. In particular, there is provided a method for treating disorders involving abnormal cellular Fc receptor mediated immune reactions in human or animal patients which comprises administering to a human or animal in need of such treatment an amount of said exogenous polypeptide which is effective in adjusting the Fc receptor mediated regulation of the immune reaction in a manner suitable to overcome said disorder.

Examples reported in the specification of the present application demonstrate that a exogenous Fc-reagent can augment or inhibit immunity to antigen, in particular antigen associated with a disease related to the immune response. The publications of Cowan et al., which provide the data for Examples 1, 2, 3 and 7 of the present application, harmonize contradictory results described in the prior scientific art and present the concept of exogenous Fc receptor systemic immunotherapy, for example: (1) The augmentation of inhibition of ADCC to SRBC antigen by SPA in vitro was shown to be due to the relative ratio of antibody, immune comples and Fc receptor (1979, *Biomedicine* 30, 23), (present application Example 1). (2) SPA augments or inhibits immunity e.g. delayed hypersensitivity to antigen e.g. SRBC in vivo (1979, *Biomedicine* 30, 241), (present application Example 2). (3) The mitogenic and antimitogenic activity of SPA is due to the Fc receptor valence (1979, *Biomedicine* 31, 220), (present application Example 3). (4) A review article explaining the use of exogenous Fc receptors to alter endogenous Fc receptor mediated immunity (1980, *Biomedicine* 32, 108). (5) systemic SPA Immunotherapy of rat adenocarcinoma (1982, *Biomedicine* 36, 29). (present application Example 7); this type of rodent laboratory animal model is a prototype for human clinical trials (Ravin, A., et al., 1988, *Can. Res.*, 48, 2245).

Furthermore, the basic principles of immunology, immunotherapy, Fc receptor mediated immunity to antigen and participating molecules e.g. antibody, cytokines, immune complex, Fc receptors are present in humans, veterinary and laboratory animals (*Basic & Clinical Immunology*, (sixth edition, 1987) D. P. Stites, J. D. Stobo and J. V. Wells (eds.), Appleton & Lange: Los Altos, Cal.); (*An Introduction To Veterinary Immunology*. (1977), Ian R. Tizard. W. B. Saunders Company, Philadelphia); (*The Merck Veterinary Manual*. (sixth edition, 1986, C. M. Fraser (ed.), "The Immune System" pp. 409–424, Merck & Co., Rahway, N. J.); *The Merck Manual of Diagnosis and Therapy*, (thirteenth edition, 1977), R. Berkow and J. H. Talbott (eds.), "Immunology Allergic Disorders", pp. 183–156, Merck & Co., Rahway, N. J.).

As further stated in *The Merck Manual of Diagnosis and Therapy*, (thirteenth edition, 1977). R. Berkow and J. H. Talbott (eds.), "Immunology Allergic Disorders", pp. 183–156. Merck & Co., Rahway, N.J.) a delayed hypersensitivity reaction to antigen is important in the defense against malignant cells and infectious agents, e.g. disease related to the immune response. Example 2, of the present specification demonstrates the complete enhancement or inhibition of a delayed hypersensitivity reaction to an antigen, e.g. SRBC, by administration of an exogenous Fc receptor e.g. SPA was dependant on the concentrations of participating immune molecules, e.g. antigen, SPA. Furthermore, Fc receptor mediated immunity to antigen is constant for all antigens, e.g. SRBC, cancer cells (*Structure and Function of Fc Receptors* (1983), A. Froese and F. Paraskevas (eds.), Marcel Dekken, Inc.: New York.), (Cowan, F. M., et al., 1980, *Biomedicine* 32, 108), (Kerbel, R. S. and Davies, A. J. S., 1974, *Cell* 3, 105).

Clinical tests are available in the clinical medical art for detecting Fc receptor mediated immunity to antigen e.g. ADCC, delayed hypersensitivity, immune complex and mitogenic activity; indeed, Examples 1, 2 and 3 of the present specification are examples of such tests. (Agnello, V., p. 178, 1980, *Manual of Clinical Immunol-* ogy. Rose, N. R. and Friedman H. (eds.), American Society For Microbiology, Washington D.C.); *The Merck Manual of Diagnosis and Therapy*, (thirteenth edition, 1977), R. Berkow and J. H. Talbott (eds.). "Immunology Allergic Disorders", pp. 183-156, Merck & Co., Rahway, N. J.) Cowan, F. M., et al., 1979, *Biomedicine* 31, 220.

In order to yet further illustrate the objects and advantages of the present invention, the following examples will be given as illustrative, and not limitative.

EXAMPLE 1

Effect of SPA on the Antibody Dependent Cellular Cytotoxicity (ADCC) of Lymphocytes Towards a Cellular Antigen, e.g. CRBC in the Presence and Absence of CRBC-Antibody Immune Complex The ADCC assay is a clinical test for detection of immune complex and can be used to detect Fc receptor activity.

Materials and Methods

BALB/c mice 6 to 8 weeks old and weighing 20 grams, were obtained from Charles River Breeding Labs. Inc., Wilmington, Mass. The animals were housed in plastic cages and fed water and Purina Lab Chow ad libitum.

Immune complexes were prepared using rabbit anti-sheep red blood cell (SRBC) sera (Grand Island Biological Company, Grand Island, N.Y.) and SRBC (Flow Lab., Rockville, Md.). Briefly, a 3% suspension of SRBC was incubated for 30 minutes at room temperature with an equal volume of rabbit anti-SRBC sera at the lowest dilution that did not cause agglutination of SRBC. The incubation mixture was washed three times in phosphate buffered saline (PBS) (0.01M), pH 7.2, and a volume of PBS equal to the size of the pellet was then added. The sensitized SRBC were freeze thawed 3 times, centrifuged in the cold at $700 \times g$ for 10 minutes, and the supernatant containing the immune complexes collected.

Spleen leukocytes were prepared by cutting spleens into small pieces and passing the minced preparation through a 80 mesh stainless steel screen to obtain a mono dispersed population of cells. Spleenic erythrocytes were eliminated following an incubation with 0.83% NH4Cl for 10 minutes at room temperature. The cells were washed 3 times with cold RPMI-1640 media and adjusted to $1 \times 10^8$ cells/ml in RPMI 1640 containing 10% heat inactivated fetal calf serum (FCS). Splenic cells were separated on a Ficoll-Hypaque density gradient as follows: Four ml of spleen cells ($10^8$/ml) were added to a 15 ml conical centrifuge tube and underlayed with 5 ml of 12 parts 14% Ficoel (Pharmacia, Piscataway, N.J.). The gradient was centrifuged at $400 \times g$ for 30 minutes at room temperature. The interface cells were collected, washed 3 times with RPMI-1640+10% FCS for the ADCC assay or rosette assay.

The ADCC assay, developed by Perimann et al. (*J. Immunol.* (1972) 108, 558) was used with some slight modifications. Briefly, 0.2 ml of a 1% suspension of washed chicken red blood cells (CRBC) (Flow Laboratories, Rockville, Md.) in PBS was added to 0.2 ml RPMI-1640+10% FCS plus 200 uCi of 51 cr (Na2-CrO4 Amersham/Searle, specific activity 50-400 mCi/ml, Arlington Hts., Ill.) and incubated at 37° C. (degrees Centigrade) for 1 hour in a shaking water bath. Following incubation, the labeled CRBC were washed twice with RPMI-1640+10% FCS and adjusted to $2 \times 10^6$ cells/ml.

For the rosette assay gradient separated spleen lymphocytes from BALB/c mice were suspended in RPMI-1640+10% FCS media at a concentration of $10^6$ Cells/015 ml and placed in $12 \times 75$ mm polypropylene test tubes follow, by 0.1 ml of a 3% suspension of washed SRBC. The tubes were centrifuged at $250 \times g$ for 10 min and incubated at 4 C. for 1 hour. Following incubation, the cell pellet was gingerly resuspended and 0.2 ml of formaldehyde (2% solution in PBS) and 0.2 ml of toluidine blue (0.2% in PBS) (Eastman Chem. Co., Rochester, N.Y.) were added to each tube. At least 200 lymphocytes were immediately counted. Lymphocytes binding three or more erythrocytes were considered positive rosettes.

In selected assays, mouse lymphocytes were pretreated with a variety of agents to determine their effects on the production of rosettes. In general $2 \times 10^6$ lymphocytes were incubated with either various doses of SPA (Pharmacia Fine Chemicals, Piscataway, N.J.), immune complexes, rabbit anti-SRBC sera (1:2), or combinations of these agents for 1 hour at 4 C. The lymphocytes were washed 3 times with RPMI-1640+10% FCS prior to incorporation in the rosette assay.

Depending upon the desired assay, splenic lymphocytes ($2 \times 10^7$ total cells) were incubated with either varying doses of SPA, immune complexes, rabbit anti-CRBC sera (Microbiological Associates, Bethesda, Md.) (1:100 dilution) or combination of these agents for 1 hour at 4° C. prior to incorporation into the ADCC assay. After washing the cells 3 times with RPMI-1640+10% FCS, $10^7$ lymphocytes in 1 ml were added to 50 ul of labeled CRBC ($1 \times 10^5$ cells) in $12 \times 75$ mm polypropylene test tubes, providing an effector: target ratio of 100:1. The tubes were vortexed and incubated for 18 hours at 37° C. in a humidified incubator containing 5% CO2. Following the incubation period, 1 ml of cold RPMI-1640 media was added to each tube to stop the reaction and the tubes were centrifuged at $800 \times g$ for 10 minutes. The supernatants were decanted and counted for 51 cr release in a gamma scintillation counter. The specific 51 cr release was determined by dividing the mean values of quadruplicate test samples by the maximum release of 51 cr obtained from freeze thawing labeled target cells 4 times. Controls for spontaneous 51 cr release included labeled CRBC incubated in media minus the presence of splenic lymphocytes.

Results

Effect of SPA on rosette formation. The incubation of rabbit anti-SRBC sera with $10^6$ normal mouse lymphocytes at 4 C. for 1 hour resulted in 60% rosette formation as compared to 10% rosette formation among normal lymphocytes not exposed to sera. Addition of 0.2 ml of prepared immune complexes to the incubation mixture of mouse spleen cells and rabbit hemolysin reduced the percentage of rosette forming cells from 60% and 32%. However, the addition of varying doses of SPA to the assay system restored the number of rosetted cells back to 63%, slightly above normal levels. Normal mouse lymphocytes incubated alone with either SPA or immune complexes provided a level or rosette formation (10%) comparable to that observed for the lymphocyte control. Employing a standard rosetting in which target cells were sensitized with rabbit anti-SRBC rather than effector cells, 61% rosetting was achieved. Pre-incubation of mouse spleen lymphocytes with 0.2 ml of prepared immune complex abrogated the extent of rosetting to 29%. The addition of 25 ug of SPA to the above pre-incubation mixture of immune complexes and effector cells again restored rosetting to normal levels (i.e. 58%).

Effect of SPA and lymphocyte absorption on ADCC. Mouse spleen lymphocytes ($2 \times 10^7$) were incubated for 1 hr at 4° C. with 1 ml of rabbit anti-CRBC at a dilution of 1:100. Following 3 washes, this cell preparation lysed 30% of 51 cr labeled CRBC ($2 \times 10^5$) during an overnight incubation at 37° C. The addition of prepared immune complexes to the first incubation mixture in concentrations as low as 25 ul reduced the level of 51 cr release from 30% down to control lymphocyte levels of 10%. Pre-incubation of the effector cells with the immune complex prior to exposure with rabbit anti-CRBC gave similar results. Addition of 10 ug of SPA to a mixture consisting of mouse spleen lymphocytes and immune complexes with or without rabbit anti-CRBC sera completely abolished the inhibitory effect of immune complexes on the ADCC assay and raised the level of 51 cr release to greater than 60%. This enhanced activity above the positive sera controls (i.e. 30%) was due to neutralization of endogenous immune complexes contained within the rabbit anti-CRBC sera with increasing numbers of mouse splenocytes which neutralized its inhibitory activity by removing immune complexes, thereby increasing ADCC activity. Since commercially prepared rabbit anti-CRBC sera was found to contain significant amounts of immune complexes, it was unnecessary to add an exogenous source of immune complexes for the purpose of inhibiting ADCC. Various doses of SPA were also capable of promoting the activity of rabbit anti-CRBC sera with a subsequent increase in ADCC activity. In the absence of sera, the addition of SPA or prepared immune complexes to mouse spleen cells at the highest concentrations used in the assay, did not provide for any increase in ADCC activity relative to control levels of 10%.

EXAMPLE 2

Effect of SPA on the Primary Delayed Hypersensitivity (DH) Response in Mice Toward a Cellular Antigen, e.g. SRBC, Depending on the Dose of the Antigen Materials and Methods Animals. DBA mice 6 to 8 Weeks Old and weighing 20 grams were obtained from Charles River Breeding Labs Inc., Wilmington, Mass. The animals were housed in plastic cages and fed water and Purina Lab Chow ad libitum.

Antigens. Sheep red blood cells (SRBC) (Flow Laboratories, Rockville, Md.) were washed 3 times in phosphate buffered saline (PBS) (pH 7.2, 0.01M) before use. Mice were sensitized on day 1 with varying doses of SRBC either intravenously (iv) or intradermally (id). A challenge dose of $10^8$ SRBC was always administered id in the right hind foot pad on day 4.

Staphylococcus Protein A. SPA was dissolved in PBS and stored frozen ($-20°$ C.) in aliquots of 5 mg/ml. SPA was administered in 0.2 ml of buffer via an intraperitoneal (ip) injection. Animals were treated with varying doses of SPA (Pharmacia Fine Chemicals, Piscataway, N.J.) on day 1 together with the sensitizing dose of SRBC, or on day 4 with a challenging dose of SRBC. SPA was also given on a multidose schedule on days 1 through 4.

Radioisotopic foot-pad assay. The assay was performed according to the procedure of Paranjpe et al. (J. Nat. Cancer Inst., 1972 48, 563). Briefly, I125 labeled bovine sera albumin (New England Nuclear, Boston, Mass.) containing 100,000 cpm in 0.2 ml of PBS was injected ip into each animal along with the challenge dose of antigen on day 4. The mice were sacrificed 24 hours later and the test and control hind feet were amputated at the middle third of the tibia, and counted in a gamma scintillation counter. Results were expressed as a foot count ratio according to the following formula: cpm test foot minus background/cmp control foot minus background Controls and experimental values of foot count ratios represent the mean of quadruplicate experiments each containing 10 animals per group.

Results

Mice sensitized with SRBC (i.e. $10^8$ id or $10^5$ iv) on day 1 followed by a challenge dose of the same antigen ($10^8$ SRBC id) on day 4 demonstrated a significant DH response as measured by a radioisotope foot-pad assay on day 5. Sensitization with $10^8$ SRBC id revealed a foot pad ratio of 2.4 and animals immunized with $10^5$ SRBC iv had foot-pad ratios of 3.1, while animals immunized with $10^8$ SRBC iv had a DH response of 1.6. at the time of assay (day 5). Nonsensitized control animals receiving a challenge dose of $10^8$ SRBC id on day 4 had foot pad ratios of 1.4 at the time of assay (day 5). SPA injected as a single dose ip on day 4 or a multiple doses on days 1–4 could inhibit a DH responses to SRBC at both the $10^8$ id or $10^5$ iv sensitizing doses. The inhibition by SPA was dose dependent and closely associated with the challenge doses of SRBC ($10^8$ id on day 4). SPA at a 1 mg dose caused little inhibition of DH (P 05) when given on day 1, yet 1 mg of SPA given with the challenge dose of SRBC on day 4 completely abrogated DH for the $10^8$ ip or $10^5$ iv sensitizing doses.

A dose of $10^8$ SRBC injected iv on day 1 caused a paralysis of DH with a foot count ratio of 1.6. However, SPA injected on day 1 or days 1–4 was capable of ameliorating the above suppressed DH response. This latter response was dependent on the dose of SPA employed and was associated with the sensitizing dose of SRBC ($10^8$ iv on day 1). SPA at 1 mg dose given on day 4 was unable to promote an increase in DH; however, a 1 mg dose of SPA given on day 1 with a sensitizing dose of $10^8$ SRBC iv almost completely restored the DH response to 2.8.

SPA showed no inherent ability to activate a DH response without prior exposure to antigen. Pre-treatment with 1 mg SPA for four days prior to challenge, ($10^8$ SRBC id) did not increase DH above negative control levels (i.e., 1.4 foot count ratio) observed in animals receiving no sensitizing dose of antigen. No toxic effects in animals treated with SPA were observed in this test.

In the present test, SPA could augment or inhibit: DH to SRBC in mice while remaining within the limits of that normally would be elicited by varying the dose or the route of a SRBC injection. SPA given with the challenge dose of SRBC (i.e., $10^8$ SRBC, id, day 4) inhibited DH in mice sensitized with SRBC at concentrations and routes of injection optimal for DH responses (i.e., $10^8$ id or $10^5$ iv, day 1). The administration of SPA with a sensitizing dose of SRBC, which normally caused a paralysis of DH (i.e., $10^8$ SRBC iv, day 1), was capable of reversing an inhibited DH response with a concomitant increase in DH. Daily doses of SPA (i.e., days 1-4) could either de-repress paralyzed DH responses or suppress active DH showing that the amount of antigen employed in the sensitizing dose directly affects the changes in DH ascribed to SPA. This phenomena may possibly be interpreted as follows:

Fc cellular receptors and immune complexes have been found to be factors influencing the immune response. Communication between different cell populations is well established for antigen specific immune regulation involving thymus helper cells (TH) and thymus suppressor cells (TS) containing systems. Immune complexes possess both Fc antibody portion and antigen. Immune complexes cross linking Fc receptors on regulatory cells or antigen presenting cells, e.g. macrophages to antigen receptor on effector cells might exert specific immune communication.

The injection of $10^8$ SRBC iv to induce DH paralysis, possible promoted an increase in circulating antigen which subsequently complexed with antibody thereby forming higher concentrations of immune complexes. The SPA daily dose experiment indicates that immune complexes may influence DH in a concentration dependent fashion (i.e., selection of TH at lower concentrations and TS at higher concentrations). SPA enhances DH when given with a greater than optimal sensitizing dose of antigen. At antigen doses optimal for eliciting DH, SPA had either no effect or inhibited DH.

EXAMPLE 3

Suppressive Effect of MSPA on DNA Synthesis

Materials and Methods

Animals. Balb/c mice 6 to 8 weeks old and weighing 20 grams were obtained from Charles River Breeding Lab., Wilmington, Mass. The animals were housed in plastic cages and fed water and Purina Lab Chow ad libitum.

Spleen leukocytes. Spleen leukocytes were prepared by cutting spleens into small pieces and passing the minced preparation through a 80 mesh stainless steel screen to obtain a mono-dispersed population of cells. Splenic erythrocytes were eliminated following an incubation with 0.83% NH4Cl for 10 minutes, at room temperature. The cells were washed three times with cold RPMI-1640 media and adjusted to $3.3 \times 10^6$ viable cells/ml in RPMI-1640 containing 10% heat inactivated fetal calf serum (FCS).

Preparation partial tryptic digests of Staphylococcus Protein A. 5 mg SPA (Pharmacia Fine Chemicals, Piscataway, N.J.) was suspended in 0.6 ml of 1% trypsin solution (w/v) made up in RPMI-1640 media and adjusted to pH 8. The SPA trypsin solutions were incubated at 30° C. for varying periods of time. At the end of the digestion period 0.6 ml FCS was added to inhibit the trypsin and the sample frozen.

Leukocyte stimulation. Mouse splenic leukocytes ($5 \times 10^5$/well, in 150 ul of RPMI-1640+10% FCS were added to 5 microtiter plates. The mitogens were added at final concentrations optimal for eliciting mitogenic response: concanavalin A (con A), 5 ug/ml, (Miles, Elkhart, Ind.), Lipopolysaccaride (LPS), 10 ug/ml (DIFCO Detroit, Mich.) and SPA, 100 ug/ml. Following a 12 hour incubation at 37° C. in a humidified incubator containing 5% CO2 100 ug of trypsin-cleaved SPA in a 25 ul of 1% trypsin and FCS was added to each test well. The cells were allowed to incubate for 72 hours before adding 1 uCi of 3H thymidine (act. 6.7 ci/m ml). The cultures were incubated for an additional 18 hours and harvested on a MASH II unit (Microbiological Association, Bethesda, Md.). Experimental value were obtained by the mean of quadruplicate samples performed on two separate occasions.

Results

Tryptic digest of SPA (100 ug per well), digested, with 1% trypsin at 30° C. for 10, 30 and 60 minutes were added to mouse splenic leukocytes 12 hours after stimulation with the mitogens Con A and LPS. The mitogenic activity measured using a 3H-thymidine incorporation assay. The ability to suppress DNA synthesis in mitogen stimulated cells increased gradually as the trypsin digestion time increased. The SPA preparations were at no time cytotoxic as determined by trypan blue exclusion. Intact SPA did not effect the mitogenicity of the other mitogens. Compared to assays performed in trypsin free media (Con A 114.000 cpm; LPS 47.000 cpm) trypsin at the same concentration as the SPA digests, added simultaneously with the mitogens was highly inhibitory for the mitogenic activity of Con A (38.000 cpm, 72% inhibition) but not LPS (45.000, 5% inhibition). However, when added 12 hours post mitogen, as in our assay, the trypsin was only slightly inhibitory for the mitogens Con A (99.000 cpm, 15% inhibition) and LPS (45.000 cpm, 5% inhibition). At no time was trypsin alone capable of completely eliminating the actions of the mitogens. Mitogenicity was completely suppressed only when SPA was digested under conditions favorable for yielding SPA fragments containing only one Fc receptor site. SPA digested for 18 hours at 30° C. with 1% trypsin had no remaining mitogen suppressive activity.

EXAMPLE 4

Methods of Treatment Using Exogenous Fc Receptors

Treatment of conditions characterized by abnormal levels of circulating immune complexes. A patient with a condition due to abnormal levels of circulative immune complexes (bacterial, viral, fungal, or parasite infection, immune or atuo-immune disorders, graft, or cancer); thus abnormal Fc receptor mediated immune response (ADCC, delayed hypersensitivity, phagocytosis) and/or immune regulation T helper cell or T suppressor cell function, is treated as follows: (1) Serum is taken from the patient and the concentration of circulating immune complexes is determined therein by means of an immune assay. (2) In an in vitro assay it is determined the Fc receptor of which source (example SPA Fc receptors) and which concentration of the Fc receptor is most effective at neutralizing the respective circulative immune complex. Note: The type of Fc receptor receptor. The does of Fc receptor which has been determined receptor. The dose of Fc receptor which has been determined as described above is administered to the patient. The determination of the dose is frequently repeated as needed and the dose is adjusted accorrding to the respective test results.

EXAMPLE 5

Treatment of Disorders Related to Abnormal Gene Expression (viral infection, cancer, auto-immune disease) with Monovalent Fc Receptor Cells infected with virus, malignant cells or autoimmune cells undergoing blastogenesis are incubated in a 3H thymidine assay (as used in example 3). Varying concentrations of monovalent Fc receptor from different sources (example monovalent SPA-receptor) are added to the assay system and an effective dose of monovalent Fc receptor is calculated which is sufficient to repress abnormal gene expression. The daily dose of monovalent Fc receptor which has thus been determined is administered to the patient.

EXAMPLE 6

MSPA and SPA Anaphylactiod Reactions

Results

Unsensitized guinea pigs weighing 500-600 g (Summit view Farms, Belvidere, N.J.) were injected i.c. with varying doses of SPA and monvalent SPA (MSPA) (Pharmacia, Piscataway, N.J.). Four animals were used for doses <1 mg and two animals for each higher dose >2 mg for both SPA and MSPA. As in earlier studies 0.5 mg SPA caused considerable toxicity and 1 mg or more of SPA produced uniformly lethal systemic anaphylaxis (Table 1). The 1 mg and 2 mg doses of SPA caused death within 10 minutes while 3 mg SPA produced violent convulsions and death within 3 minutes. In contrast to SPA, MSPA demonstrated only mild toxicity and no lethal anaphylaxis at the 0.5, 1, 2 or 3 mg doses (Table 1).

| Dose | Toxicity SPA, MSPA | |
|---|---|---|
| | # Animals | Lethal Anaphylaxis |
| 0.5 mg SPA | 4 | 1 |
| 1 mg SPA | 4 | 4 |
| 2 mg SPA | 2 | 2 |
| 3 mg SPA | 2 | 2 |
| 0.5 mg MSPA | 4 | 0 |
| 1 mg MSPA | 4 | 0 |
| 2 mg MSPA | 2 | 0 |
| 3 mg MSPA | 2 | 0 |

EXAMPLE 7

Reducing Effect of SPA on Lung Metastases in Rats A Prototype for Clinical Trials

Materials and Methods

Animals. Fisher F344 female rats, approximately 2 months old and weighing 120-140 grams, were housed in plastic cages, five to a cage, and fed water and Purina Lab Chow ad libitum.

Tumor. The ascites form of the 13762 rat mammary adenocarcinoma (obtained through Mason Research Institute, Worchester, Mass.) was used. The ascites tumor was maintained by peritoneal transfer at approximately weekly intervals. The creamy ascites fluid was generally free of any contaminating red blood cells. The tumor cells were all washed twice in phosphate buffered saline (PBS) pH 7.2 prior to use.

Tumor Injecting. Animals administered the tumor cells: intravenously (iv) received a total dose of $1 \times 10^6$ cells per 0.5 ml via the tail vein. All the animals in any given experiment, received their injections from the same tumor cell suspension.

SPA Preparation and Injection. SPA was prepared by suspending 5 mg of material into 1 ml of PBS. The SPA was subsequently adjusted to 5000 ug, 500 ug, and 50 ug/ml aliquats. Animals were injected intraperitoneal (ip) with one of these concentrations on a daily basis for eleven days starting one day after an iv injection of viable tumor cells. The one day interval between tumor cell and SPA injection allowed the tumor cells to stabilize their distribution into the body.

Lung Metastases. (Counting of Nodules) Twelve days following the injection of $1 \times 10^6$ tumor cells iv, the animals were sacrificed and their lungs insufflated by needle injection into the trachea with a 15% solution of India ink. The lungs were then excised en bloc and fixed in Bouin's solution for one day prior to counting. The colonies appeared as white, round nodules against a black surface and were easily counted with the naked eye on all five lung lobes. Pulmonary deposits never exceeded more than 200 colonies at the dose of cells inoculated.

Statistics. The results were statistically evaluated using student's t-test. Each experimental dose group contained ten rats.

Results

Normal F344 rats injected iv with $10^6$ adenocarcinoma cells in ascites form on day one, produced a large number of well-defined white nodules on the surface of the lung. Infusions of the lungs on day 12 was optimal for quantitative purposes producing a means number of 114 metastatic growths.

The administration of SPA on days 1 through 11 at a dose of 10 ug was totally ineffective in reducing the number of surface colonies. Treatment of rats injected with tumor on day 1, with 100 ug or 1000 ug of SPA for eleven days, inhibited the development of pulmonary metastases in a dose related manner. In addition to a significant reduction in the number of lung metastases, the metastatic nodules present in the animals given 1 mg SPA daily appeared, on day 12, to be generally smaller and better defined than the central or low dose (i.e. 10 ug, 100 ug SPA) groups.

In other experiments the median survival time of animals treated with 1 mg SPA was significantly prolonged over untreated control 15 animals. A median survival time of 34 days was observed in the SPA treated group as compared to 19 days for the untreated animals.

Example 7, just described, discloses the inhibition of the development of pulmonary metastases in rats which is a prototype for human clinical trials by systemic treatment with SPA (Staphylococcus aureus protein A). All of the animals were injected with $10^6$ adenocarcinoma cells on day 0; the rats in Groups 1, 2 and 3 were given daily doses of 10, 100 and 1000 micrograms, respectively, SPA i.p. on days 1 through 11; all animals were sacrificed on day 12 and the number of metastatic colonies were counted for all animals; the results are tabulated below:

| Group # | Dose SPA (ug) | Number of Metastases |
|---|---|---|
| 1 | 10 | 120 |
| 2 | 100 | 84 |
| 3 | 1000 | 38 |
| 4 | control | 118 |

The third column, labeled "Number of Metastases" lists the average number of metastases for animals in each group.

EXAMPLE 8

Amino Acid Homology: HIV p17, Thymosin *P224* 1 and SPA

HIV p17

_Glu—Ile_ _Thr_ _*****_ _Glu—Gln_

Ile  Lys—Asp  Lys—Glu  Glu—Glu  Asn

Thymosin *P 224*1

_Thr—Thr_ _Leu_ _*****_ _Ala—Gln_

Ile  Lys—Asp  Lys—Glu  Glu—Glu  Asn

SPA

Ala_Asp—Asn_ _Phe—Asn_ _*****_Tyr_ _Ile—Leu—His

Lys  Lys—Glu  Glu

The 8 specific amino acids that are homologous to HIV gag protein located between amino acid residues 92-109 and thymosin amino acid residues 11-28; when aligned with the known sequence of the bacterial Fc receptor, SPA fragment B amino acid residues 120-137, reveal amino acid homology between the three proteins. Fifty percent (4 of 8) amino acid residues homologous for HIV p17 gag protein, and thymosin are homologous to SPA fragment B. Seventy-five percent (6 of 8) amino acid residues are common to all three proteins if variation of the four SPA-Fc receptor regions and related amino acid residues Ile and Ala are considered. In the above amino acid sequences, an asterisk (*) represents a nonhomologous amino acid.

Numerous papers published in peer reviewed scientific journals corroborate a "rational basis" for utility of the present invention. These are:

(1) Bender et al, *J. of Infectious Diseases*, Vol. 152, No. 2, August 1985, pp. 409-412. This paper demonstrates that FcR mediated immunity is defective in AIDS patients and this defect correlates with mortality rate.

(2) Tavares et al, *Cancer Research*, Vol. 47, Jun. 15, 1987, pp. 3190-3194. ATZ is the drug of choice for use and therapy of AIDS and other retrovirus disease in humans and animals. Feline Leukemia virus (FeLV) associated immunodeficiency is very similar to human AIDS and is an animal model for AIDS therapy. As in human AIDS, ATZ in the FeLV model can reduce but not eliminate the retrovirus in chronically infected patients.

(3) Engelman et al, *Cancer Detection and Prevention*, Vol. 10, 1987, pp. 435-444. Demonstrates that SPA-FcR used extracorporeally, or injected (exactly as is claimed in the present application) can induce remission of FeLV retrovirus infection and/or associated malignancies. This constitutes greater efficacy, and thus utility, in the FeLV animal model for AIDS using SPA therapy than is achieved by AZT, the current drug of choice for retrovirus disease. (AZT does not affect malignancy or achieve complete remission of chronic retrovirus infection.)

(4) Engelman et al, *American J. of Pathology*, Vol. 118, March 1985, pp. 367-378. Demonstrates regression of various pathologies associated with retrovirus infection using SPA Fc-reagent therapy.

(5) Boyle et al, *BioTechnology*, Vol. 5, July 1987, pp. 697-703. This paper teaches the use of bacterial Fc receptors, such as Protein A found on the surface of, or secreted by, Staphylococcus aureus. Reactions with human IgG are mentioned.

(6) Lange et al, *AIDS*, Vol. 1, No. 3, 1987, pp. 155-159. This paper shows that decline in IgG antibody reactivity to HIV core protein 17 is an early marker of disease progression. Thus, declining or absent IgG reactivity is associated with AIDS.

(7) Nauts, International Symposium on Biological Preparations in the Treatment of Cancer, London 1977, *Develop. Biol. Standard*, Vol. 38, 1978, pp. 487-494. This paper shows that bacterial toxins have induced remissions of malignancies in humans, and a bacterial vaccine was used to treat cancerpatients as early as 1893 by the author's grandfather.

(8) Messerschmidt et al, *Federation Proceedings*, Vol. 41, No. 3, Mar. 1, 1982, p. 325. This paper shows Protein A injected into dogs has antineoplastic activity for a variety of tumors (9) Richner et al, "In Vitro Adsorption of Colon Cancer Sera over Staphyloccus Protein A: Lymphocyte Stimulation by Leakage of Absorbance," *Klin Wochenschrift*, Vol. 65, 1987, pp. 353-358. This paper is concerned with the leakage of SPA from extracorporeal columns.

(10) Sinclair et al, "Immunoregulation by Fc Signals," *Immunology Today*, Vol. 8, No. 3, 1987, pp. 76-79. This paper demonstrates that Fc receptors are the central mechanism of immune regulation. Therefore, the status of Fc receptors as to other immune participants may influence the immune response to immune antigens.

(11) Messerschmidt et al, *J. of Clinical Oncology*, Vol. 6, No. 2, February 1988, pp. 203-212. This article describes a multicenter human clinical trial of SPA-FcR extracorporeal immunotherapy with the following results and comments:

(a) Circulating immune complexes have been shown to be involved in the regulation of a variety of immune phenomena, are known to be present in cancer patients and are responsible for much of the cancer-associated immunosuppression. See page 203, introduction and paragraph #1.

(b) Patients with histologically confirmed malignant disease who had failed conventional therapy were eligible for the study. See page 204, the paragraph under the heading "Patients."

(c) Antitumor effects for a variety of malignancies were noted in 24% of patients overall, and 47% of patients with AIDS associated Karposi's sarcoma responded favorably.

(d) The paper concludes: "The present trial demonstrates that immunoadsorption treatment of plasma over a protein A-silica column can be performed safety in the outpatient setting and <u>results in antitumor effects</u>."(Underlining added.)

(e) The clinical trial protocol was reviewed and approved by the Food and Drug Administration and Institutional Review Boards. See page 204, the paragraph under the heading "Treatment Procedure."

This human clinical data clearly demonstrates that SPA immunotherapy has antineoplastic activity for a variety of tumors that failed to respond to conventional therapy. Messerschmidt et al, at page 210, bottom right, state that they cannot rule out elution from the column of protein A. In other words, the authors recognize that the favorable results observed in their study may have resulted from SPA infusion which, of course, is the treatment principle of the present application.

(12) Rhodes, *Nature*, Vol. 265, Jan. 20, 1977. This paper teaches that the expression of Fc receptors on circulating human monocytes is substantially increased in individuals with solid malignant tumors. It is suggested that the change in monocyte surface characteristics occurring in malignant disease exert a net inhibitory effect on antitumor immunity.

(13) Patrone et al, *JNCI*, Vol. 67, No. 4, October 1981, p. 803. This paper discusses the inhibition of Fc receptors in cancer patients.

(14) Rhodes et al, *JNCI*, Vol. 66, No. 3, March 1981, p. 423. This paper teaches that macrophage FcR function is decreased in cancer patients.

(15) Ilfeld et al, *Breast Cancer Research and Treatment*, Vol. 7, 1986, pp. 181-186. This paper shows that patients with metastic breast cancer had significantly elevated FcR levels.

(16) Roccatello et al, *Immunology Letters*, Vol. 9, 1985, pp. 53-56. This paper demonstrates that FcR function is reduced in human autoimmune diseases.

(17) Frank et al, *The New England J. of Medicine*, Vol. 300, No. 10, Mar. 8, 1978, pp. 518-523. Defective reticuloendothelial system FcR function is shown in patients with systemic lupus erythematosus (autoimmune disease).

(18) MacKinnon et al, *Arthritis and Rheumatism*, Vol. 30, No. 5, May 1987, pp. 498-506. Monocyte Fc-receptor function in rheumatoid arthritis is altered by rheumatoid factor.

(19) Bansal et al, *Cancer*, Vol. 42, No. 1, 1978, pp. 1-18. Ex vivo treatment of a colon carcinoma patient with SPA-FcR results in: "Improvement in the general condition of the patient, decrease in tumor size, healing of ulcerated areas on the surface of the tumor and absence of generalized intraperitonical metastasis" (p. 17, second paragraph).

(20) Ray et al, *Clin. Exp. Immunol.*, Vol. 42, 1980, pp. 308-314. This paper describes the selective removal of myeloma IgG and autoimmune antibodies from patient's plasma by SPA-FcR extracorporeal immunoadsorption which prolong the lives of terminal patients.

(21) Terman et al, *Science*, Vol. 209, Sep. 12, 1980, pp. 1257-1259. Describes antineoplastic effects of SPA-FcR extracorporeal perfusion treatment of dogs with mammary adenocarcinomas in enhancing the efficacy of conventional chemotherapy when the treatments are combined in a chemo-immunotherapeutic approach.

(22) Terman et al, *New England J. of Medicine*, Vol. 305, No. 20, Nov. 12, 1981, pp. 1195-1200. This relates to the achievement of partial remission using SPA-FcR extracorporeal perfision in three of five breast adenocarcinoma patients who had relapses while undergoing conventional therapy.

(23) Kinet, et al, *European J. Clinical Invest.*, Vol. 16, 1986, pp. 50-55. Plasma of twelve patients presenting with a metastic mammary adenocarcinoma was perfused ex vivo over SPA-FcR. The plasma of seven patients was treated with FcR active SPA (group A) while five patients were treated with SPA where the Fc binding capacity was destroyed (group B). In the SPA-FcR negative group B all five patients experienced progression of bone and/or liver metastic lesions. In the SPA-FcR positive group A three patients exhibited partial regression, three patients had no progression of disease, with only one patient experiencing increased size of one bone metastic lesion. Kinet et al suggest, based on this study, that Fc-binding capacity of protein A is responsible for the tumoricidal response. (See Table 2, page 52.)

(24) Bertram et al, *Cancer Research*, Vol. 45, September 1985, pp. 4486-4494. SPA-FcR extracorporeal perfusion is shown to have an antineoplastic activity for breast cancer and astrocytoma patients.

Collectively these articles corroborate a rational basis for utility of the present invention for the treatment of diseases related to the immune response, wherein abnormal Fc receptor mediated immunity to antigen contributes to the pathology or symptom of said disease, for example:

The Tarvares et al publication (2) teaches that FeLV provides an animal model for human AIDS therapy. The Engleman et al article (3) shows that the treatment of the present invention is effective in treating FeLV and collective these articles demonstrate that SPA systemic immunotherapy, the treatment of the present invention, has greater efficacy against FeLV than ATZ, the current drug of choice for retroviral disease. Since, Bender et al (1) shows that Fc receptor mediated immunity is defective in AIDS patients, there is a "rational basis" for concluding that the treatment of the present invention has utility in the treatment of human AIDS.

A "rational basis" can also be shown for the treatment of human malignancies according to the methods of the present invention. The Messerschmidt et al article (11), and a number of additional cited publications, establish the efficacy of extracorporeal treatment with SPA of human malignancies. Ray, P. K., et al., (1982, *Cancer Research* 42, 4970) demonstrates the efficacy of the extracorporal (ex vivo) treatment of rat mammary adenocarcinoma which is exactly the same disease treated by SPA Fc receptor injection in Example 7 of the present application. Engleman et al (3) shows the efficacy of both ex vivo and injection SPA immunotherapies for feline AIDS and associated malignancies. Terman et al (21) and Messerschmidt et al (11) demonstrate the antineoplastic action of both methods for canine malignancies such as canine mammary adenocarcinoma. These results in animal models are consistent with diseases related to the immune system in the *The Merck Veterinary Manual* which correspond with human diseases listed in *The Merck Manual*. Ainsworth et al., (1988, *Cancer*, 61, 1945) also demonstrates that ex vivo therapy with a form of SPA is useful for such adenocarcinomas in humans. Kinet et al (23) provides evidence that the efficacy of ex vivo SPA therapy for human mammary adenocarcinoma is Fc receptor dependent as is predicted for SPA systemic immunotherapy, the method of the present application. Ex vivo and in vivo systemic, e.g. oral or parenteral, SPA immunotherapies are not two different drugs, but different methods of administering the same drug, both involving a Fc receptor mediated immunotherapeutic mode of action. It follows, therefore, that ex vivo SPA human clinical, veterinary and laboratory animal data can be used to further supports the "rational basis" for the utility of SPA systemic immunotherapy for the treatment of neoplasts in humans and animals.

A hypothesis for Fc receptor mediated pathogenesis and therapy of retrovirus disease, e.g FeLV and HIV, provides a further "rational basis" for exogenous Fc receptors systemic immunotherapy for the treatment of retrovirus disease. Immune deficiency does not adequately explain all the observed immune pathological sequelae associated with HIV infection. Zolla-Pazner and Sidhu 1983 and Edelman and Zolla-Pazner (1983). *FASEB J.*, 3, 22) have hypothesized that the complexities of the immune system are reflected in the immunological aberrations associated with HIV infection; therefore, AIDS is a syndrome with symptoms of immune hyperactivation, autoimmune phenomena and immune deficiency suggestive of exaggerated normal immune regulation; and this progressive HIV induced immune dysregulation accumulates in the immune deficiency, opportunistic infections and malignancies characteristic of AIDS. Lepe-Zuniga and Mansell (1986, *AIDS RES.*, 2, 363) have postulated that AIDS constitutes a disease state wherein activation of immune response enhances susceptibility to HIV infection, destruction of T-helper cells and progression of the disease. One of the possible explanations for HIV immune dysregulation is the action of HIV viral proteins on the immune system. Edelman and Zolla-Pazner, supra.

The HIV p17 gag protein has immune cross reactivity and amino acid homology with the thymic hormone thymosin (Sarin, P. S., et al., 1986, *Science* 232, 1135) and when aligned with the known sequence of the SPA Fc receptor fragment B all three proteins contain common amino acid residues (Example 8 of the present application). HIV and SPA display common biological activity in that both inhibit Fc receptor mediated effector function. SPA can inhibit Fc receptor mediated immunity, e.g. ADCC and delayed hypersensitivity (Cowan, F. M., et al., 1980, *Biomedicine* 32, 108); and HIV infection causes defective Fc receptor mediated phagocytic effector function which correlates with the clinical course of AIDS (Bender, B. S., et al., 1985, *Infect. Dis.*, 152, 409). Inhibition of delayed hypersensitivity to antigen further contributes to the phatology of the disease (Edelman and Zolla-Pazner, 1983, *FASEB J.*, 3, 22). HIV antigenaemia and decline of IgG antibody reactive to and potential capable of neutralizing the p17 gag protein are prognostic markers for disease progression to AIDS (Lange, J. M. A., et al, 1987, *AIDS* 1, 155). The depressed Fc receptor mediated immunity associated with AIDS could be the result of humoral HIV p17 gag protein antigenaemia mimicking Fc receptor mediated immune inhibition and might be aggravated by other suppressive microbial Fc receptors, e.g. cytomegalovirus.

A HIV Fc receptor viral protein dysregulating Fc receptor mediated immunity could prove disastrous to the host immune response if viewed in the context of the immune model for self-nonself discrimination of immunoregulation by Fc signals proposed by Sinclair and Panoskaltsis (1987, *Immunol. Today* 8, 76) and/or Fc receptor mediated HIV cellular infectivity (Homsy J. et al., 1989, *Science* 244, 1357) and the action of suppressive exogenous Fc receptors on immune regulation (Cowan, F.M., et al., 1980, *Biomedicine* 32, 108). Furthermore, circulating HIV p17 gag protein mimicking an IBF (Sinclair and Panoskaltsis 1987, *Immunol. Today* 8, 76) could amplify antigen specific "antibody feed back" suppression of Fc receptor mediated immunity and/or inhibit Fc receptor effector activity. T-helper cells produce soluble factor(s) that prevent "antibody feed back" suppression (Sinclair and Panoskaltsis 1987, *Immunol. Today* 8, 76). As T-helper cell numbers decline in AIDS (Bender, B. S., et al., 1985, *Infect. Dis.*, 152, 409) such an Fc receptor mediated immune suppressive mechanism would become more pronounced. A HIV Fc receptor viral protein "jamming" Fc receptor mediated immune regulatory signals could provide the virus with "immunological stealth" and contribute to the immune dysregulation and dysfunction associated with retrovirus infection.

Immune complexes precipitated from the sera of HIV positive patients are infectious in cell culture (Homsy J. et al., 1989, *Science* 244, 1357). HIV Fc receptor mediated macrophage infectivity in addition to anti-HIV antibody (Takeda, A., et al., 1988, *Science* 242,580) may proceed via HIV p17-Fc receptor engaging antigen-antibody immune complexes Fc antibody portions. These HIV-immune complexes aggregates could be phagocytized infecting macrophages or incorporate the macrophage's function as a antigen presenting cell to infect T-helper cells. Fc receptor mediated antigen specific presentation of HIV, preferentially infecting CD4 positive T-helper cells responding to antigen would involve all monocyte mediated antigen specific T cell response. Individuals infected with HIV often display elevated immune complex levels (Bender, B. S., et al., 1985, *Infect. Dis.*, 152, 409) and impaired immunity of both T and B cells to antigens requiring monocytes while T cell response to monocyte independent mitogens remains relative intact (Zolla-Pazner 1983, *FASEB J.*, 3, 22). HIV Fc receptor mediated antigen specific T-helper cell clonal infection could explain, in part, how HIV incorporates Fc receptor mediated immune mechanisms, to infection of only a small percentage of T-helper cells (Fauci, A. S., 1988, *Science* 239.617), which are responding to antigen, and induces the devastating immune suppression to antigen associated with AIDS.

Furthermore, Fc receptor mediated internalization of immune complexes is similar to the ligand endocytosis described for a variety of cell membrane associated receptors and Fc receptor mediated endocytosis is operable even when the Fc receptor expression is on non-lymphoid cells (Mellman, I., et al., 1988*J. Cell Sci. Suppl.*, 9, 45). In addition to cells of the immune system Fc receptor are located on the cell membranes of a variety of other cell types, including central and priferal nervous system tissues (Vedeler, C. A., 1987, *J. Neuroimmunol.*, 15, 207). Fc receptor mediated HIV cellular infection may extend beyond immune cells involving other Fc receptor positive cell types, possibly explaining in part the diverse tissue trophism and pathology associated with HIV infection.

AIDS has been associated with defective production and activity of cytokines (Fauci, A. S., 1988, *Science* 239,617). Cytokines e.g. interferon enhance Fc receptor expression amplifying Fc receptor mediated immunity (Cowan, F. M., et al., 1982, *Biomedicine* 36,29) and Fc receptors engaged by antibody Fc constant region ligand function as signal-transducing molecules which promote gene expression and production of cytokines (Cassatella, M. A., et al., 1989, *J. Ex. Med.*, 169, 549) indicating a Fc receptor-cytokine immune regulatory loop. Thus, the inhibition of Fc receptor mediated immune response associated with AIDS could explain the reduced cytokine activity.

A potential relationship exists between the immune suppression associated with HIV and the SPA immunotherapy induced remission of an AIDS-like condition in the FeLV model (Engelman, R. W., et al., 1987, Can. Detect. Prev., 10, 435) based on known amino acid homology and possible common biological activity between HIV p17 gag protein, and the Fc receptor regions of SPA. This relationship may be of importance in understanding the immune suppression associated with and the design of therapy for AIDS. A HIV Fc receptor-like viral protein "jamming" Fc receptor mediated immune regulatory signals could provide the virus with "immunological stealth" and contribute to the immune dysregulation and dysfunction associated with retrovirus infection. SPA ex vivo or systemic immunotherapy, the method of the present invention, is the only drug which has cleared a chronic retrovirus infection and achieved remission of associated malignancies in an animal model for AIDS (Engelman, R. W., et al., 1987, Can. Detect. Prev., 10, 435). The interaction between retrovirus and Fc receptors is well documented in the medical art, thus provides additional "rational basis" for exogenous Fc receptor systemic immunotherapy for the therapy of retroviral disease.

The patent art contains further "rational basis" for Fc receptor immunotherapy. Pollard U.S. Pat. No. 4,464,164 teaches that the ex vivo extracorporal Fc-reagents can be used to retard the growth of neoplasts in subject mammals, and the utility for the use of an extracorporal Fc-reagent to retard the growth of neoplasts is established by reference to published prior art (col. 1, lines 9-19). Sedlacek et al U.S. Pat. No. 4,479,934 teaches the injection of complement or antibody Fc-reagents (endogenous Fc receptors) for the treatment of immune complex disease. Thus, both the medical literature and the patent art establish a clear "rational basis" for the utility of systemic exogenous Fc receptor immunotherapy, the method of the present invention, for the treatment of disease related to the immune response wherein, immune complex disease and abnormal immunity to antigen contribute to pathology.

From the preceding description it is clear that the present invention comprises a method for treating a disease related to the immune response, wherein abnormal Fc receptor mediated immunity to antigen contributes to the pathology or symptoms of the disease; and an immune complex disease, often associated with diseases related to the immune response, in a patient suffering from such a disease condition, which method comprises locally or systemic administering to said patient an effective amount of at least one Fc-reagent comprising an exogenous e.g. microbial polypeptide which has in its molecule at least one site possessing a binding capability for the Fc-portion of antibody or antigen-antibody immune complex said Fc-reagent further possessing greater binding affinity for antigen-antibody immune complex than for free antibody. The method further comprises administering the Fc-reagent to adjust the ratio of endogenous antibody and antigenantibody immune complex to Fc receptors so that Fc-receptor mediated immunity to the disease antigen(s) is restored to within normal physiological limits.

What is claimed is:

1. A method of immunotherapy for treating the pathological delayed hypersensitivity response to antigen of an immune complex disease condition caused by an antigen-antibody immune complex in a patient suffering from such a disease condition, which method comprises locally or systemically administering to said patient an effective dose of at least one Fc reagent comprising an exogenous polypeptide selected from bacterial polypeptides or leukocyte polypeptides, said polypeptide having at least one site which binds to the Fc-portion of said antigen-antibody immune complex, said antigen-antibody immune complex being susceptible to such binding.

2. The method of claim 1 wherein said immune complex disease condition is abnormal immunity to antigen.

3. The method of claim 1 wherein said immune complex disease condition is abnormal Fc receptor mediated immunity to antigen.

4. The method of claim 1 wherein said immune complex disease condition is abnormal antibody dependent cellular cytotoxicity to antigen.

5. The method of claim 1 wherein the Fc reagent is a IgG leukocyte Fc receptor-like polypeptide.

6. The method of claim 1 wherein the Fc reagent is a bacterial Fc receptor-like polypeptide.

7. The method of claim 1 wherein the Fc reagent is a IgG bacterial Fc receptor-like polypeptide.

8. The method of claim 1 wherein the Fc reagent is Staphylococcus aureus protein A.

9. The method of claim 1 wherein the Fc reagent is a fragment of Staphylococcus aureus protein A molecule.

10. The method of claim 1 wherein the dose of Fc reagent is flexible, individualized and varies with different phases of the immune complex disease, and from patient to patient, being raised or lowered according to alterations in the course of the disease or the development of undesirable effects.

11. The method of claim 1, further comprising determining the level of immune complex circulating in said patient and calculating the dose of said Fc reagent suitable to neutralize the determined level of circulating immune complex.

12. The method of claim 1, wherein the disease condition is caused by a bacterial, viral, fungal or parasite infection.

13. The method of claim 1, wherein said binding of the Fc reagent of the Fc-portion of the antigen-antibody immune complex prevents substantial subsequent binding of said complex to cellular Fc-receptors without binding substantial amounts of free antibodies formed in response to the antigen.

* * * * *